United States Patent [19]

Fitzgerald et al.

[11] Patent Number: 5,054,313
[45] Date of Patent: Oct. 8, 1991

[54] CONTROL CIRCUITRY FOR VISCOSITY SENSORS

[75] Inventors: John V. Fitzgerald, Metuchen; Teresa M. Walsh, Lawrenceville; Frank J. Matusik, Piscataway; John Stone, Vincentown, all of N.J.; Edmond Dougherty, Strafford, Pa.; John Batton, New York, N.Y.

[73] Assignee: National Metal and Refining Company, Ltd., Metuchen, N.J.

[21] Appl. No.: 554,285

[22] Filed: Jul. 17, 1990

[51] Int. Cl.⁵ ........................................... G01N 11/14
[52] U.S. Cl. ..................................................... 73/59
[58] Field of Search ................................. 73/54, 59, 60

[56] References Cited
U.S. PATENT DOCUMENTS 3,762,429 10/1973 Fitzgerald et al. ................. 137/92
4,524,610 6/1985 Fitzgerald et al. ..................... 73/59

Primary Examiner—Robert Raevis
Assistant Examiner—Shu-Cheng Kau
Attorney, Agent, or Firm—Arthur L. Lessler

[57] ABSTRACT

Electronic control circuitry for obtaining precise inline process control data as to viscosity of fluids over a wide viscosity range, with high tolerance of ambient noise and vibration. An electromechanical transducer with an oscillating sensor is immersed in a flowing liquid, with the power required to sustain predetermined oscillation parameters being a measure of viscosity-density product. The gain of a variable gain amplifier which provides positive feedback to sustain oscillation is controlled in response to the integrated error signal output of a comparator which compares a DC value corresponding to the RMS amplitude of mechanical oscillation with a DC reference value. The monitoring of RMS amplitude rather than peak amplitude (as is done by a phase-sensitive sample-and-hold arrangement in the prior art), coupled integration of the error signal, results in a great improvement in immunity to ambient noise and vibration. Other features includes automatic calibration and temperature compensation whereby viscosity at a desired temperature can be determined even though the measurement is made at different temperature.

8 Claims, 5 Drawing Sheets

CONTROL CIRCUITRY FOR VISCOSITY SENSORS

BACKGROUND OF THE INVENTION

This invention relates to an apparatus and method for substantially improving the viscosity measuring performance of viscometers and rheometers of the oscillatory type when used in the presence of ambient noise and/or vibration. The invention is especially suitable for, but not limited to, use with inline viscometers in process control applications; and is particularly effective in viscometer and rheometer devices employing oscillation sensors of the types disclosed in U.S. Pat. Nos. 4,524,610, 4,566,181 and 4,754,640, as well as U.S. patent application Ser. No. 07/348,695.

In process control applications in manufacturing or processing plants, pump, machinery and pipe vibration adversely affects the accuracy of viscosity measurement by oscillatory viscometers and rheometers; devices which are otherwise capable of high precision. In a factory, viscosity of fluid materials is often measured at high temperatures and pressures while the materials are passing through vibrating pipes. This environment produces noisy electronic signals in most instrumentation, including oscillatory (also known as vibratory) viscometers, and gives rise to erratic and erroneous readings.

When the viscosity of the fluid is high, e.g. 1,000 to 1,000,000 centipoise and more, the amplitude of the signal produced by a vibratory viscometer is generally relatively high in comparison to the background noise caused by factory vibrations. Thus the effects of noise and vibration are generally tolerable in instruments intended for measurements at such high viscosity levels.

On the other hand, when the viscosity range is low, e.g. 1 to 100 centipoise, as it is for many liquids such as solvents, fuels and monomers, mechanical disturbance from pumps, nearby moving vehicles and machinery can produce erroneous signals that seriously interfere with the viscosity measurement. These conditions are so severe that inline viscosity measurements at these low values have frequently been viewed as having no significant benefit.

Accordingly, an object of the present invention is to provide an apparatus and method capable of accurate inline measurement of viscosity in the presence of extraneous noise and vibration.

SUMMARY OF THE INVENTION

As herein described, there is provided a control circuit for an oscillatory viscometer having a transducer assembly including a sensor having a portion adapted for immersion in a fluid a viscous property of which is to be determined, a drive means responsive to a drive signal for causing the sensor to mechanically oscillate, and a detector means for generating a sensor movement signal corresponding to the movement of the sensor.

The circuit has a variable gain amplifier with an input terminal coupled to the detector means for receiving the sensor movement signal, and an output terminal coupled to the drive means for providing the drive signal thereto. The gain of the variable gain amplifier has a value determined by a gain control signal applied to a gain control terminal thereof.

The transducer assembly and variable gain amplifier form a primary oscillator loop for causing the sensor to mechanically oscillate. AC to DC conversion means is coupled to the detector means for generating at an output terminal thereof a varying DC signal having a value corresponding to the amplitude of mechanical oscillation of the sensor.

Comparator means is coupled to the output terminal of the conversion means for generating a difference signal corresponding to the difference between the value of the varying DC signal and a reference signal having a value corresponding to a desired amplitude of mechanical oscillation of the sensor;

Integrator means is coupled to the comparator means for integrating the difference signal to generate the gain control signal, which is coupled to the gain control terminal of the variable gain amplifier. The integrator means responds to changes in the difference signal sufficiently rapidly so that the sensor is caused to oscillate with an amplitude corresponding to the value of the reference signal.

IN THE DRAWING

ADVANTAGES OF THE INVENTION OVER THE PRIOR ART

Figure 1:
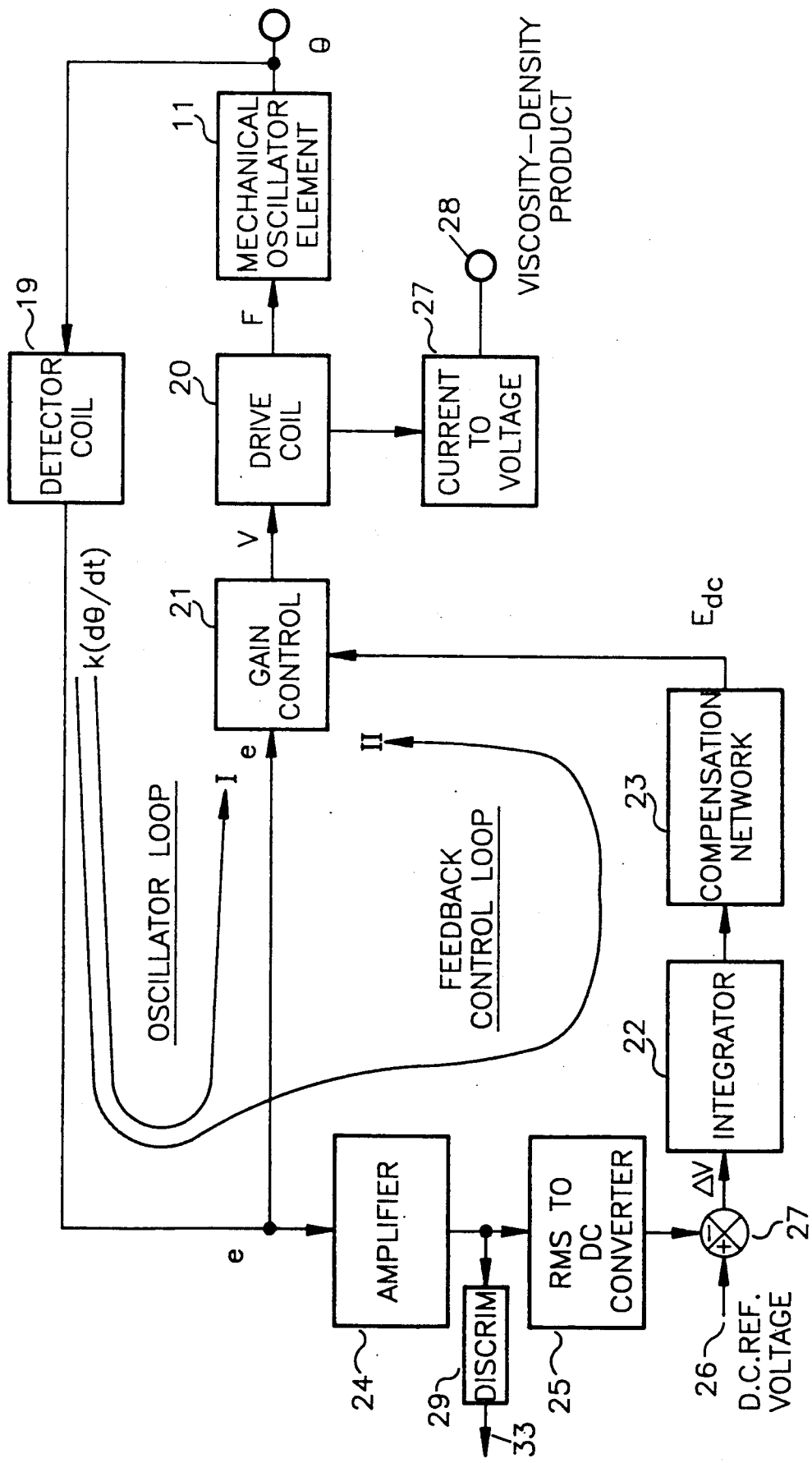
FIG. 1 is a block diagram showing a control circuit for a vibratory viscometer, incorporating an analog integrator for reducing vibration interference, according to a first embodiment of the invention.

An improved vibratory viscometer according to the present invention incorporates certain vibration rejection circuitry and microprocessor based averaging software. These features substantially improve the performance of viscometers referred to in U.S. Pat. Nos. 3,382,706; 3,712,117; 3,710,614; 3,762,429; 4,488,427 in the presence of ambient vibration and/or noise, even under severe factory vibrational conditions, at viscosities in the range of one (1.0) to over one million (1,000,000) centipoise.

According to another aspect of the invention, the viscometer is automatically calibrated when its sensor tip is dipped in a standard, i.e. a fluid of known viscosity. Previously one had to immerse the sensor in a standard liquid having known viscosity and then manually select and adjust electronic components until the readout coincided with the viscosity of the standard. Since normally one calibration per decade of scale was used, errors could occur at parts of the decade range remote from the viscosity value of the sample. However, the automatic calibration feature employed in the arrangement of the present invention facilitates use of an increased number of samples, providing calibration points at closer intervals throughout the range to be measured, thus resulting in increased accuracy of measurement.

In order to measure viscosity over many scale decades, as is required, for example, when monitoring a polymerization process, it was previously necessary to utilize autoranging techniques to automatically shift the viscometer from one scale to another. As a result, prior measurement accuracy in such situations was only ±2% of full scale, so that for example near the upper end of a scale a 900 centipoise (cP) measurement would be accurate to ±18 cP; while at the lower end of that scale a 90 cP measurement would be accurate to the same ±18 cP or only ±20% of the measured value. To obtain better accuracy in the prior art, the scales were overlapped.

The automatic calibration arrangement of the present invention provides a great improvement, as it yields an accuracy of ±2% of the reading (over the entire range of the instrument) rather than ±2% of full scale as in prior art instruments.

The prior art inline viscometers described in the aforementioned patents are not suitable for factory applications because of their inability to adequately resist vibrations and because of viscosity readout discrepancies due to scale overlap and lack of uniform accuracy as a percentage of the measured value. Oscillation type viscometers constructed in accordance with the teachings of this application are significantly improved over oscillation type viscometers which are currently commercially available.

The Dynatrol Viscosity Control ("Dynatrol") viscometer, sold by Automation Products, Inc., 3030 Max Roy, Houston, Tex. 77008, utilizes converters which determine viscosity using a selected one of a series of four different oscillating sensors, each covering a range of two centipoise decades, with overlapping ranges. A separate sensor is required for temperature. In order to isolate the Dynatrol from factory vibrations a special stand and jack for bracing to the floor is recommended by the manufacturer.

One of the Dynatrol inline viscometers is claimed to be impervious to factory vibrations. It requires a slip-stream and a ½ inch process connection into and out of the sample chamber. By controlling the length of by-pass pipe for taking the sample from the process pipe line, the sensor (which oscillates at a frequency of 125 Hz.) is mechanically isolated from the process pipe line. The installation of such an arrangement is expensive and is not always practical.

An oscillation type viscometer, known for many years as the "Bendix Viscometer", is produced by ABB Process Analytic Combustion Engineering, P. O. Box 831, Lewisburg, W. Va. 24901. The sensor oscillates in the longitudinal mode. The range of viscosity-density product is 0–50 centipoise×grams/cc with attenuation factors of ×1, ×10, ×100 and ×1000. Combustion Engineering claims that the viscometer should measure with an accuracy of ±2% of range and states that "a lot of vibration will disturb measurement".

The Sofraser Process Viscometer utilizes a flexural vibration type sensor for viscosity measurement and a separate probe for temperature measurement. The sensor employs a driver coil and a detector coil. A constant amount of power is supplied to the driver coil in a closed loop circuit to cause the sensor to oscillate in a flexural resonance mode at about 300 Hz. The amplitude of oscillation varies with the viscosity of the fluid in which the sensor tip is immersed. It is claimed by the Haake division of Fison Instruments, Inc. of 24911 Stanford Avenue, Valencia, Calif. 91355 that viscosity values are not affected by the vibrations of other processing equipment because the sensor always oscillates at its resonance frequency. Four sensors are required to cover the ranges 1 to 1000; 10 to 10,000; 100 to 100,000; and 1000 to 1,000,000 centipoise. Accuracy is claimed to be ±0.5%.

GENERAL DESCRIPTION

Oscillation Amplitude Control Circuitry

An oscillatory viscometer according to a preferred embodiment of the invention employs a sensor which is caused to oscillate in a torsional mode by a driver coil. A pickup coil detects the torsional vibration. A control circuit couples the output of the pickup coil to the input of the driver coil and causes the sensor to torsionally oscillate at its mechanical resonant frequency, at a predetermined constant amplitude; the amount of power supplied to the driver coil to maintain the constant amplitude of oscillation when the sensor tip is immersed in a fluid being a measure of the viscosity-density product of the fluid. This type of oscillatory viscometer is known in the prior art.

Prior art viscometers of the aforementioned type typically use a sample-and-hold type amplitude sampling circuit to determine the amount of increase or decrease in power that must be supplied to the driver coil to maintain the set amplitude of vibration. This type of sampling is phase dependent and overly sensitive to detected voltage phase changes. Mechanical noise upsets the phase of the detector voltage easily and causes disturbances in the system.

According to the invention, an ac/dc to RMS (root-mean-square) convertor and an integrator amplifier are utilized to detect the amplitude of oscillation of the sensor tip and control the power increase or decrease required to maintain the predetermined amplitude of oscillation. The integrator guarantees that under steady-state conditions the error voltage corresponding to the difference between the desired constant amplitude and the actual amplitude of oscillation will be zero. This is a continuous type amplitude sampling system and is less prone to voltage disturbances than the sample-and-hold arrangement, while being immune to the phase disturbances to which the sample-and-hold arrangement is susceptible.

In the preferred embodiment compensation networks have been included in the oscillation amplitude control loop to insure adequate damping of the oscillator loop characteristic in response to either signal or external mechanical disturbances. Along with this noise rejection circuitry, a high Q bandpass filter (with a passband centered at the resonant frequency of the transducer/sensor) is utilized to detect the voltage representing viscosity. The small bandwidth of transducer frequencies optimizes the filtering capability of the bandpass filter. This filter is able to reject noise frequencies and allow only the desired resonance frequency which imparts viscosity information to be processed.

Figure 2:
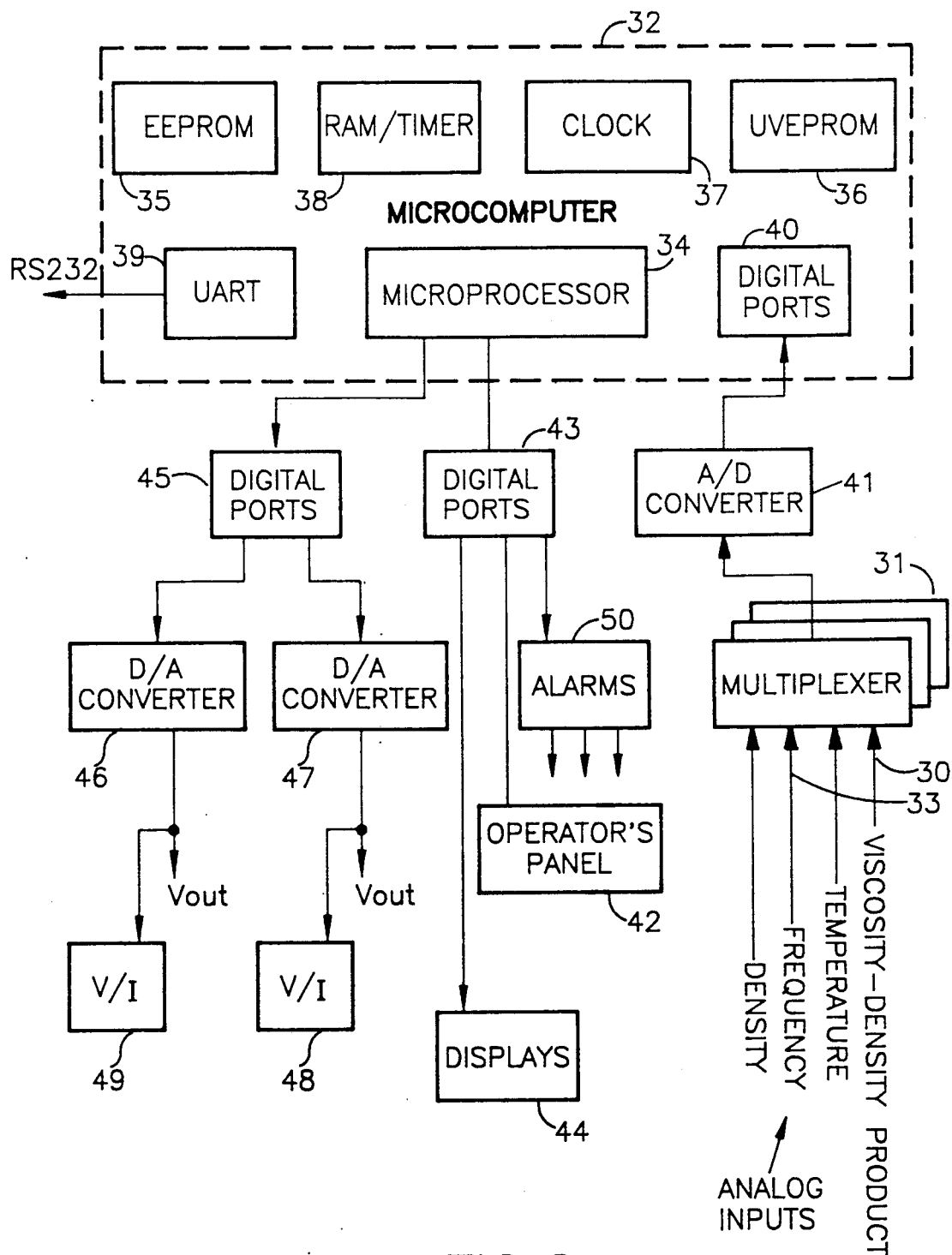
FIG. 2 is a functional block diagram of an arrangement for conversion of analog signals into digital signals and for time averaging such signals by means of microprocessor software.
Figure 3:
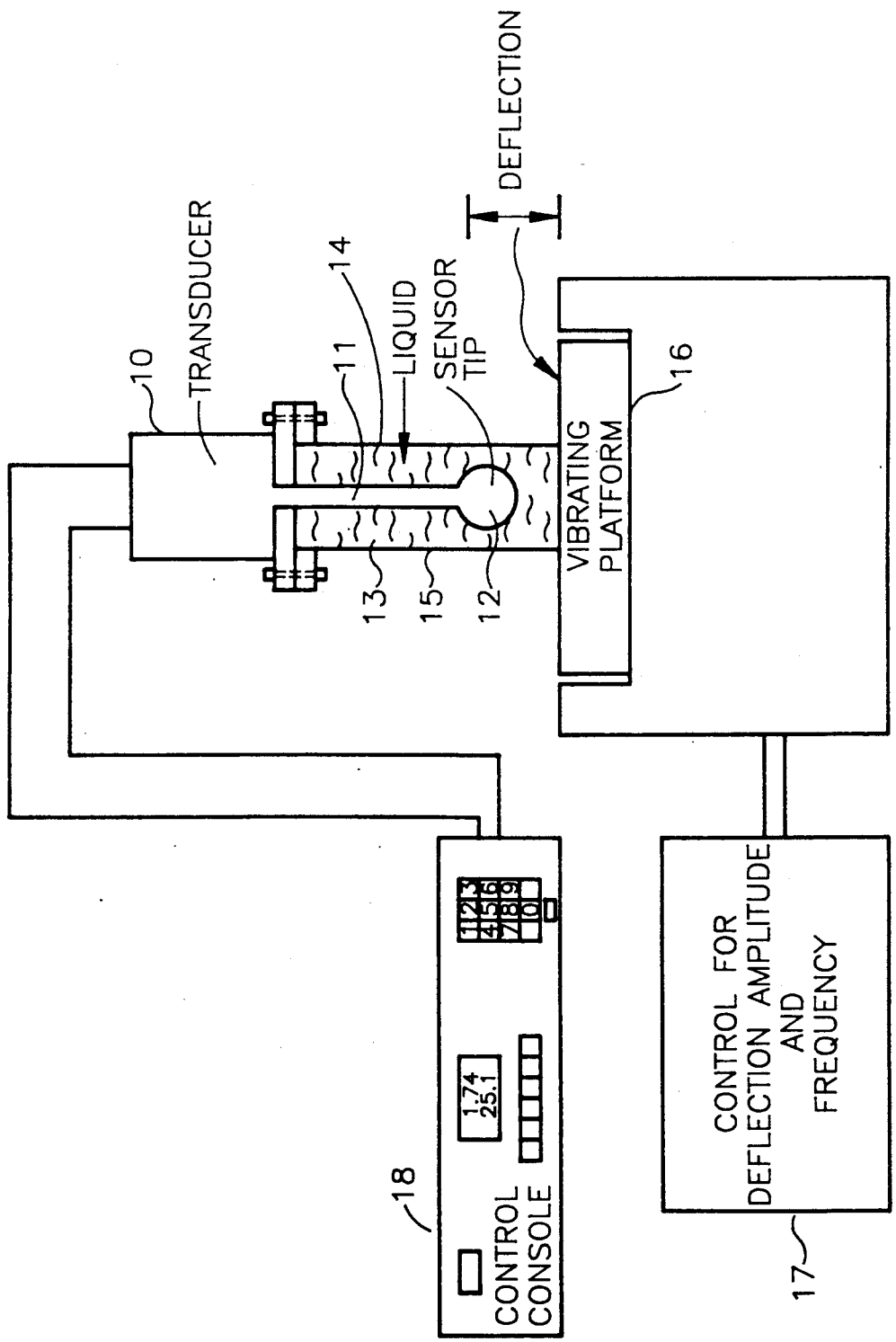
FIG. 3 is a diagram of an arrangement for vertically oscillating a viscometer transducer sensor of the torsional oscillation type immersed in a fluid, at a fixed or varying frequency so that the vertical oscillation of the viscometer simulates environmental vibration.

The improvement in resistance to vibration at low viscosities attained by a viscometer according to the preferred embodiment shown in FIGS. 1 and 2 was measured by the vibration resistance testing arrangement shown in FIG. 3. Measurements were made by the American Environments Company of Medford, N. Y.

As shown in FIG. 3, a transducer with a sensor 11 having a tip 12 is immersed in a reference liquid 13 disposed in a cylindrical container 15 which is secured to a vibratable platform 16. Deflections of the vertically vibrating platform were varied in the range of 0.00001 to 1.0 inches peak-to-peak over a frequency range of 5 to 1200 Hertz by the vibration control unit 17, while the spherical sensor tip 12 was immersed in a series of liquids with viscosities in the range of 1 to 30,000 centipoise. The capability of distinguishing true viscosity in the presence of the noisy signal background due to the vibration was determined by means of the control console 18, which contains viscometer circuitry according to the aforementioned preferred embodiment of the invention.

Performance of the viscometer arrangement of the preferred embodiment was compared with a similar viscometer lacking the previously described features of the preferred embodiment. The result of this comparison is shown in FIG. 4.

Figure 4:
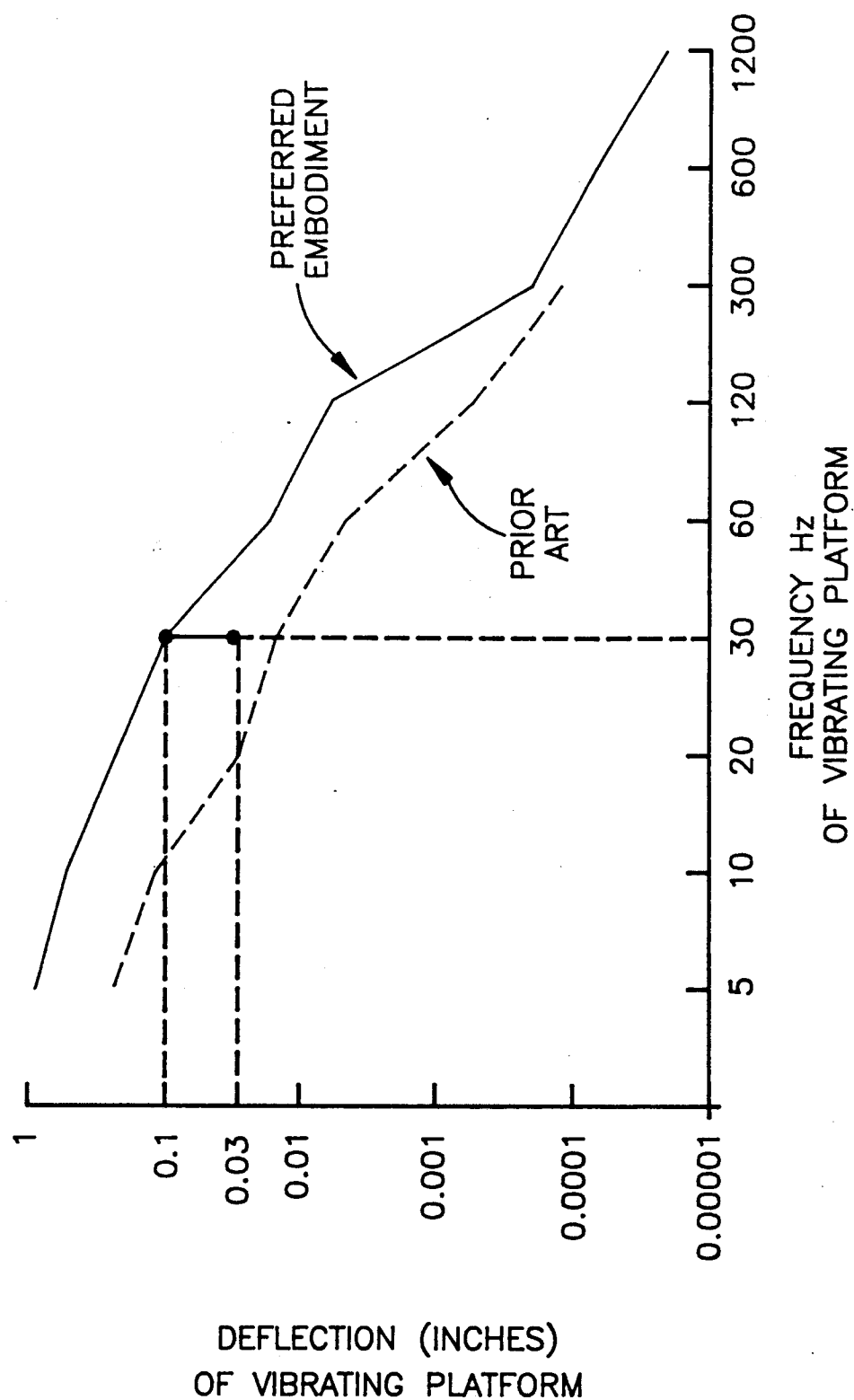
FIG. 4 is a chart comparing the resistance to vibration of an oscillatory viscometer incorporating an embodiment of the present invention with the resistance to vibration of the same viscometer without the features of the present invention.

For water, a very low viscosity liquid with a density of about 1 g/cm$^3$, the two curves shown in FIG. 4 were obtained. For each platform vibrational frequency the vertical deflection was increased until a viscosity reading of one centipoise for the water sample was barely perceptible, and the corresponding deflection value was recorded. For a viscosity measurement accuracy of ±5% the vertical deflection had to be reduced by a factor of one-third. Thus at 20° C., 30 Hertz and vertical deflection of 0.1 inch the one centipoise signal was barely perceptible; but at a vertical deflection of 0.03 inches a viscosity reading accuracy of 1.00 ±0.05 centipoise was obtained. At the 0.03 inch deflection level at 30 Hz the prior art circuitry would not indicate viscosity at all. In order to achieve a comparable ±5% accuracy, the vertical deflection must be less than 0.01 inches. Similar data were obtained when the transducer 10 was subjected to horizontal vibration.

Figure 5:
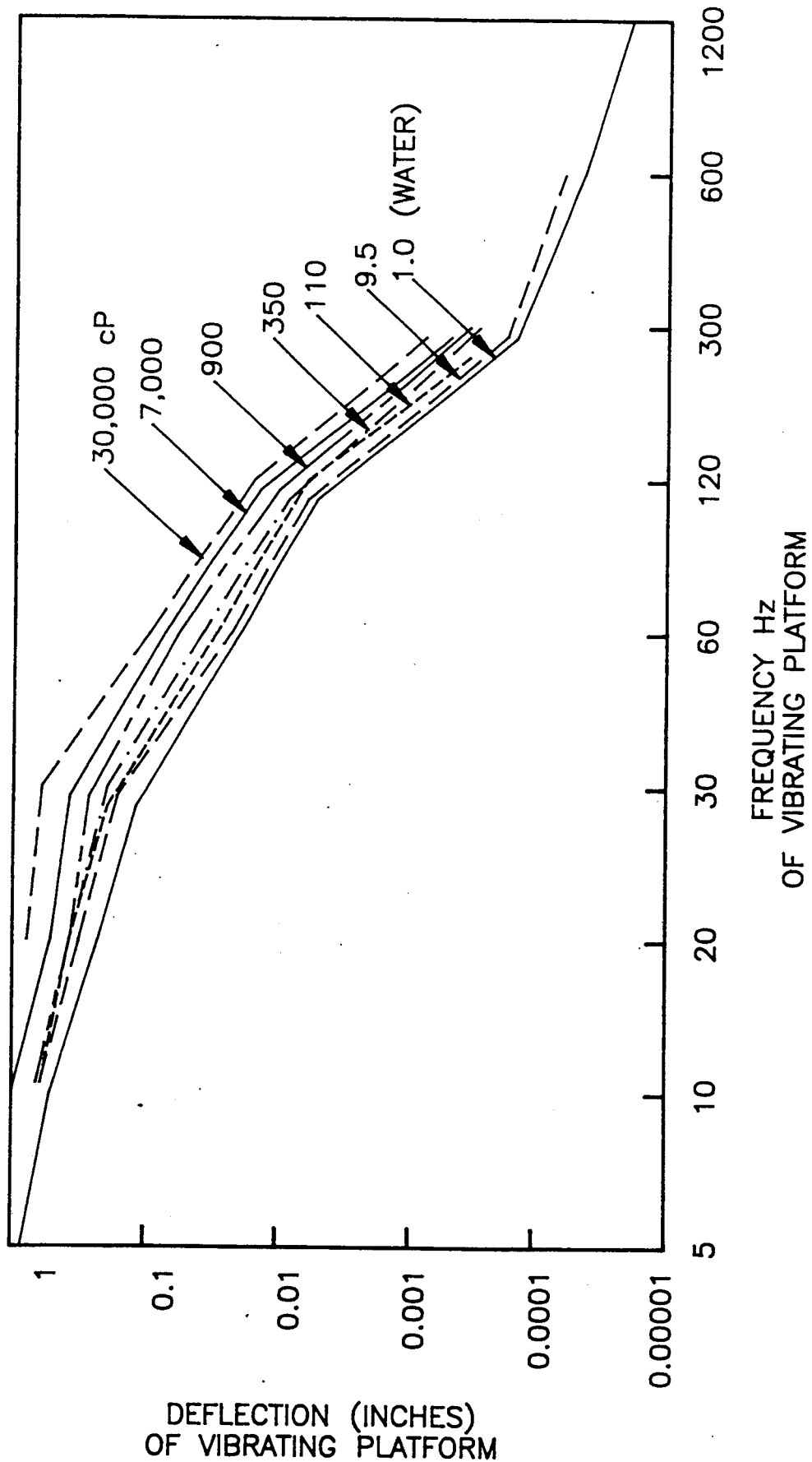
FIG. 5 is a chart showing variation of resistance to vibration with fluid viscosity.

When the viscosity of the fluid 13 was increased, the family of curves shown in FIG. 5 was obtained for the aforementioned preferred embodiment. As the viscosity increased from 1 to 30,000 centipoise the capability of the viscometer for measurement under more severe deflection conditions improved by a factor of about five.

Long Term Averaging

In the preferred embodiment, sensitivity to vibration is further reduced by averaging viscosity sample values over a user specified period of time. A computer stores a viscosity reading in a FIFO (first in first out) queue every two seconds. The queue has a capacity to hold 300 sample values, corresponding to the number of readings taken in ten minutes. After each reading the computer takes the average of all the samples collected over the time period specified by the user. The average of the readings is used as the basis for determining the viscosity.

For example, if the user wanted to average the readings over 1 minute, he (or she) would select the "average" function of the viscometer and enter, via the front panel keypad, 60 seconds as the averaging time period. From that point on, the microprocessor will calculate and display the viscosity every four seconds, with the calculation being based on the samples averaged over the previous minute. Every two seconds, a new reading is taken and stored; every four seconds a new viscosity value is determined based on the most recent minute's samples (in this case 30 samples).

The advantage of this method is that although the true time average can be taken over periods as long as ten minutes, the latest viscosity value is updated and displayed every four seconds.

Display Modes

The system can display the viscosity in a variety of modes including viscosity-density product (cP×g/cm$^3$). To obtain other display modes, viz. centiPoise or centiStokes, the density of the sample being measured is required. Density can be entered manually through the front panel keyboard or a densitometer output signal can be connected to the unit, allowing the density to be automatically read by the microcomputer. The microcomputer determines viscosity by dividing the viscosity-density product by fluid density.

Temperature Compensation

Temperature greatly affects the viscosity of a material. Software is included in the system to automatically compensate for temperature changes. The user can select the temperature to which the viscosity should be referenced. For example, assume that a known mixture has a viscosity of 1100 cP at 20° C., 1000 cP at 25° C., and 900 cP at 30° C. Assume also that it is desired that the viscosity of the mixture at 25° C. must remain as close as possible to 1000 cP. Further assume that the process temperature cannot be well controlled and varies ±10 to ±20° C. In normal operation under these conditions, the viscosity reading displayed by the unit would vary with temperature and range from 900 to 1100 cP.

If an operator or automatic control system were monitoring the viscosity, it would be difficult to determine how well the desired 1000 cP viscosity of the material was holding. However, if the user were to select, via the front panel, the temperature compensation option and request that the readings be referenced to 25° C., when the material has the proper composition its viscosity reading should always be 1000 cP, regardless of the temperature of the mixture. If in this mode the viscosity display showed a value of 700 cP, the operator (or an automatic control system) would know that the variation was due to problems with the mixture and not fluctuations due to temperature.

The temperature compensation calculation is based on a generally known formula. However, the instrument has a feature which allows the user to customize the calculation for a particular material. Via a simple set-up procedure the instrument automatically measures a particular parameter of the material that varies in a known way with temperature. The parameter is employed in the temperature compensation calculation. (If known, the parameter can also be entered directly by the user, eliminating the set-up procedure.)

Calibration

The system has a built-in computer assisted calibration routine. Through the use of the front panel, the user is able to calibrate the system throughout a user selected range of viscosities. The calibration is stored in an electrically erasable read-only memory ("EEROM").

Temperature Linearization

The microprocessor applies a linearization correction to the temperature readings supplied by the system's thermocouple.

Computer Interface

The system provides an RS-232 serial port to enable it to communicate with other computers and control systems. Software has been written for the IBM-PC (MS-DOS and PC-DOS operating systems) class of computers to communicate with the viscometer and to provide additional data processing and display capabilities.

Output Ports

The system has a number of user configurable outputs. These include a dual channel digital alarm, three voltage channels and three current channels. The alarm limits can be set by the user via the front panel. The voltage and current ranges can be set by the user.

Dual Product Design

The system has been designed so that by modifying the software, it can act as either a visco-densitometer or a rheometer. Alternatively, software for both applications can be included and selected by the user.

DETAILED DESCRIPTION

Oscillation Amplitude Control Circuitry

The servo control system shown in FIG. 1 maintains a constant amplitude of mechanical oscillation of the transducer sensor 11 and consists of two loops, viz. the primary oscillator loop I and the secondary feedback control loop II.

In the oscillator loop I the input of an electromagnetic detector coil 19 adjacent a magnetic member connected to the oscillating transducer sensor 11 provides an AC signal having an amplitude, frequency and phase reflecting the mechanical movement of the sensor 11. An electromagnetic drive coil 20 is disposed adjacent a magnetic member connected to the sensor 11 and causes the sensor 11 to oscillate in accordance with a signal applied to the drive coil 20 by the output of the variable gain amplifier 21. The amplifier 21 receives as its input signal e the output of the detector coil 19 and has a transfer function so as to provide positive feedback between the detector and drive coils, causing the sensor 11 to oscillate at its mechanical resonant frequency, which is usually on the order of hundreds of Hertz. The gain of the amplifier 21 is controlled by a gain control signal $E_{dc}$ so as to maintain a predetermined constant amplitude of mechanical oscillation of the sensor 11. The oscillator loop I and the use of a gain controlled amplifier therein to maintain a constant amplitude of mechanical oscillation are known in the prior art.

However, the secondary feedback control loop II differs from the prior art in the incorporation of an RMS to DC converter and an integrator 22 which provide improved immunity to ambient noise and vibration.

In the secondary feedback control loop II, the detector coil output signal e is converted into a DC signal which varies at a slow rate in comparison with the frequency of oscillation of the sensor 11 (i.e. a time constant hundreds or thousands of times the period of sensor oscillation), by an amplifier 24 and RMS (root-mean square) to DC converter 25.

For a sensor 11 which typically has a mechanical oscillation frequency in the range of 625-725 Hz., i.e. a period in the range of 0.0014 to 0.0016 seconds, the RMS to DC converter 25 would have a time constant in the range of 0.01 to 0.10 seconds, a 725 Hz. sensor having a preferred amplifier/RMS to DC converter time constant of about 0.02 seconds.

The output voltage of RMS to DC converter 25, which corresponds to the amplitude of mechanical oscillation of the sensor 11, is compared to a DC reference voltage 26 in a comparator 27; and the difference or error voltage $\Delta v$ is applied to the input terminal of the analog integrator 22, which preferably comprises an operational amplifier integrator of the type used in analog computers.

The integrator 22 preferably comprises an operational amplifier with a resistor-capacitor feedback network selected so that their product, i.e. the time constant $\tau$ of the resistor-capacitor network of the integrator, is in the range of 500 to 2,000 times the period of mechanical oscillation of the sensor 11 (but no greater than the maximum value at which the sensor oscillation amplitude control loop is stable); and preferably on the order of 700 times said period.

For example, with a sensor having a mechanical resonance frequency of 725 Hz./period of 0.00138 second, the time constant of the integrator should be in the range of 0.7 to 2.8 second and preferably on the order of 1.0 second. In a preferred embodiment for this sensor, the capacitor would have a value of 1 $\mu$F and the resistor would have a value of 1 M$\Omega$, for a time constant of 1.0 second.

The integrator 22 insures stable steady-state operation of the control loops I and II with an error voltage $\Delta v$ of zero in the control loop II, i.e. with no significant difference between the reference voltage 26 and the output of the RMS to DC converter 25.

If the time constant of the integrator 22 is too great the control loops are unstable and the sensor cannot be maintained at the desired constant amplitude of oscillation. If the time constant of the integrator is too small, the system is overly sensitive to ambient vibration and noise. Therefore the time constant of the integrator 22 should preferably be the maximum value with which the control loops are stable on a long term basis.

In the prior art a peak detector in the form of a phase detector type sample-and-hold circuit was used to sample the peak of the AC output waveform of amplifier 24. This prior art circuit operated by sampling the AC waveform 90° in phase after each zero crossover, on the assumption that the peak of the waveform would be at that point. This prior art arrangement, however, yields poor results in the presence of noise, which can cause troublesome variations in the phase as well as the peak value of the AC waveform at the output of amplifier 24.

The RMS to DC converter 25 provides an output which is a measure not of the peak amplitude of mechanical oscillation of the sensor 11, but rather of the RMS amplitude of mechanical oscillation, a parameter which is considerably less sensitive to ambient noise and vibration. Further, since the RMS to DC converter (which is a commercially available circuit) does not employ a phase detector, it is unaffected by phase variations in the output of amplifier 24 due to ambient noise and vibration.

The integrator circuit 22 integrates the error voltage $\Delta v$ so that the integrator output voltage corresponds to a time integral function of the error voltage. This output voltage is applied to the compensation network 23, which introduces a phase shift to compensate for phase shifts elsewhere in the control loops, so as to ensure stable operation of the system.

The output voltage $E_{dc}$ of the compensation network 23 is coupled to the gain control terminal of variable gain amplifier 21, to adjust the gain thereof so as to maintain a constant (RMS) amplitude of mechanical oscillation of the sensor 11, at a level corresponding to the value of the reference voltage 26.

The power supplied by the variable gain amplifier 21 to the drive coil 20 to maintain a constant amplitude of mechanical oscillation of the sensor 11 when immersed in a fluid, is a measure of the viscosity-density product of that fluid. The current supplied to the drive coil 20 by the amplifier 21 is a measure of the power supplied thereto, and therefore is a measure of viscosity-density product.

A sample of the current supplied to the drive coil 20 is converted to a voltage value corresponding to viscosity-density product, by the current to voltage converter 27, to provide a viscosity-density product signal at terminal 28. This signal is coupled to input terminal 30 of multiplexer 31 (FIG. 2) which is associated with the microcomputer 32.

The output of amplifier 24 is coupled to a discriminator 29, which provides an output voltage corresponding to the frequency of oscillation of the sensor 11. This frequency-indicating voltage is coupled to input terminal 33 of multiplexer 31.

The multiplexer 31 is also provided with voltage inputs corresponding to the density of the fluid whose viscosity is being determined, and the temperature of the fluid.

Microcomputer

The microcomputer 32 comprises a microprocessor (MPU) 34, electrically erasable programmable memory (EEPROM) 35, ultraviolet light erasable programmable memory (UVEPROM) 36, a clock 37, a random access memory (RAM) and timer 38, a universal asynchronous receiver-transmitter (UART) 39 which serves as a serial interface, and digital ports 40. The microcomputer operates in a manner similar to microcomputers known in the art, receiving inputs via the multiplexer 31, analog-to-digital (A/D) converter 41 and operator's panel 42 (through digital port 43); and providing outputs to the alarms 50, displays 44 and analog devices (not shown) via digital ports 43 and 45, digital-to-analog converters 46 and 47, and voltage-to-current converters 48 and 49.

The microprocessor 34 processes the viscosity-density product, density, temperature, and frequency input information to (i) provide data as to true viscosity, (ii) perform the automatic calibration function, and (iii) provide temperature compensation as previously described.

At predetermined intervals, the timer (within 38) interrupts the microprocessor 34, which then commands the multiplexer 31 to select a data channel. The A/D converter 41 is activated and the microprocessor 34 stores the digitized data in the RAM 38.

This process is repeated for each channel of data (i.e. viscosity-density product, temperature, density and frequency). The EEPROM 35 stores the calibration characteristics of viscometer. Calibration consists of reading the voltages that correspond to various known viscosity standard values. These values are stored in the EEPROM 35 as a look-up table. Parameters entered into the EEPROM 35 via the operator's panel 42 are stored there until changed by the operator through said panel. The UVEPROM 36 stores the program which provides the previously described software features of the viscometer.

The digital ports beyond the microcomputer block provide the access to the outside world. The first set of digital ports 45 provides for the digital to analog (D/A) converters 46 and 47, a series of voltage and current outputs. These outputs represent the analog inputs from the multiplexer 31. The second set of digital ports 43 provides for an LED (light emitting diode) display 44 of said analog inputs, alarms 50, and the use of a control membrane panel (operator's panel) 42.

In addition to reading the analog data channels, the MPU 34 determines if an auxiliary computer has requested data. If the auxiliary computer requests data, any data stored in RAM 38 will be transferred to the auxiliary computer via the UART 39. The UART converts the digital data into a series of pulses which can be read by the auxiliary computer's RS232 serial port.

We claim:

1. A control circuit for an oscillatory viscometer having a transducer assembly including a sensor having a portion adapted for immersion in a fluid the viscosity or viscosity-density product of which is to be determined, drive means responsive to a drive signal for causing said sensor to mechanically oscillate at the natural resonance frequency thereof, and detector means for generating a sensor movement signal corresponding to the movement of said sensor, said circuit comprising:

a variable gain amplifier having an input terminal coupled to said detector means for receiving said sensor movement signal, and an output terminal coupled to said drive means for providing said drive signal thereto, the gain of said variable gain amplifier having a value determined by a gain control signal applied to a gain control terminal thereof;

said transducer assembly and variable gain amplifier forming a primary oscillator loop for causing said sensor to mechanically oscillate;

feedback control loop amplifier means having an input terminal coupled to said detector means for receiving said sensor movement signal, and an output terminal;

an RMS to DC converter having an input terminal coupled to the output terminal of said amplifier means, for generating at an output terminal thereof a varying DC signal having a value corresponding to the RMS amplitude of mechanical oscillation of said sensor;

comparator means coupled to the output terminal of said RMS to DC converter for generating a difference signal corresponding to the difference between the value of said varying DC signal and a reference signal having a value corresponding to a desired amplitude of mechanical oscillation of said sensor;

an analog integrator coupled to said comparator means for integrating said difference signal to generate said gain control signal;

means coupled to said integrator for phase shifting said gain control signal; and means for coupling said gain control signal from said integrator to said gain control terminal of said variable gain amplifier, said integrator having a time constant sufficiently low so that said sensor is caused to oscillate at the natural resonance frequency thereof with an amplitude corresponding to the value of said reference signal.

2. The control circuit according to claim 1, wherein said RMS to DC converter has a characteristic such that the varying DC signal at the output terminal thereof varies at a slow rate in comparison with the frequency of oscillation of the sensor.

3. The control circuit according to claim 1, wherein said integrator has the maximum time constant with which said sensor can oscillate at the natural resonance frequency thereof with an amplitude corresponding to the value of said reference signal.

4. The control circuit according to claim 1, wherein said integrator comprises an operational amplifier with an input resistor and a feedback capacitor selected so that their product is in the range of 0.5 to 2 times the period of mechanical oscillation of the sensor.

5. The control circuit according to claim 4, wherein said input resistor and feedback capacitor are selected to that their product is approximately 0.7 times the period of mechanical oscillation of the sensor.

6. The control circuit according to claim 1, further comprising computer means for generating a series of viscosity-density product sample signals at predetermined time intervals, corresponding to the power supplied to said drive means.

7. The control circuit according to claim 6, further comprising computer means for repetitively averaging a predetermined number of the most recently generated sample signals, to provide a running average viscosity-density product signal.

8. A control circuit for an oscillatory viscometer having a transducer assembly including a sensor having a portion adapted for immersion in a fluid a viscous property of which is to be determined, drive means responsive to a drive signal for causing said sensor to mechanically oscillate, and detector means for generating a sensor movement signal corresponding to the movement of said sensor, said circuit comprising:

a variable gain amplifier having an input terminal coupled to said detector means for receiving said sensor movement signal, and an output terminal coupled to said drive means for providing said drive signal thereto, the gain of said variable gain amplifier having a value determined by a gain control signal applied to a gain control terminal thereof;

said transducer assembly and variable gain amplifier forming a primary oscillator loop for causing said sensor to mechanically oscillate;

AC to DC conversion means coupled to said detector means for generating at an output terminal thereof a varying DC signal having a value corresponding to the amplitude of mechanical oscillation of said sensor;

comparator means coupled to the output terminal of said conversion means for generating a difference signal corresponding to the difference between the value of said varying DC signal and a reference signal having a value corresponding to a desired amplitude of mechanical oscillation of said sensor;

integrator means coupled to said comparator means for integrating said difference signal to generate said gain control signal; and means for coupling said gain control signal from said integrator means to said gain control terminal of said variable gain amplifier, said integrator means responding to changes in said difference signal sufficiently rapidly so that said sensor is caused to oscillate with an amplitude corresponding to the value of said reference signal.

* * * * *